United States Patent
Carney et al.

(10) Patent No.: US 10,387,746 B2
(45) Date of Patent: Aug. 20, 2019

(54) IMAGE COLOR DATA NORMALIZATION AND COLOR MATCHING SYSTEM FOR TRANSLUCENT MATERIAL

(71) Applicant: Ohio State Innovation Foundation, Columbus, OH (US)

(72) Inventors: Melody Noelle Carney, Dublin, OH (US); William Michael Johnston, Pataskala, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 22 days.

(21) Appl. No.: 15/587,504

(22) Filed: May 5, 2017

(65) Prior Publication Data

US 2017/0323460 A1 Nov. 9, 2017

Related U.S. Application Data

(60) Provisional application No. 62/332,783, filed on May 6, 2016.

(51) Int. Cl.
*G06K 9/46* (2006.01)
*H04N 17/00* (2006.01)
(Continued)

(52) U.S. Cl.
CPC ............ *G06K 9/4652* (2013.01); *G01J 3/462* (2013.01); *G01J 3/463* (2013.01); *G01J 3/50* (2013.01);
(Continued)

(58) Field of Classification Search
CPC ........... G06K 9/4652; G06K 2209/055; H04N 9/045; H04N 1/60; H04N 17/002;
(Continued)

(56) References Cited

U.S. PATENT DOCUMENTS

2004/0252303 A1* 12/2004 Giorgianni ................ G01J 3/50
356/402
2005/0036668 A1* 2/2005 McLennan ........... G06K 9/4652
382/128
(Continued)

OTHER PUBLICATIONS

M.N. Carney, W.M. Johnston, A novel regression model from RGB image data to spectroradiometric correlates optimized for tooth colored shades, Journal of Dentistry (2016), 4 pages, http://dx.doi.org/10.1016/j.jdent.2016.05.011.
(Continued)

*Primary Examiner* — Qian Yang
(74) *Attorney, Agent, or Firm* — Meunier Carlin & Curfman LLC

(57) ABSTRACT

A shade selection program is disclosed that predicts the shade choice with the smallest CIEDE2000 color difference for dental composite resin restorations when given a backing and target shade. By utilizing generated regression models, a database of spectral reflectance information, and principles of Kubelka-Munk layering, a highly accurate shade selection program was designed. Additionally, a blending model for quantification of color adjustment potential was developed. Systems and methods for correlating RGB data from the VITA Linearguide 3D Master and VITA Bleached Guide 3D Master shade guides with their spectroradiometric correlates through a regression model while indicating a methodology for validation of accuracy of digital imaging systems are disclosed.

9 Claims, 11 Drawing Sheets

(51) Int. Cl.
   *H04N 1/60* (2006.01)
   *G01J 3/50* (2006.01)
   *G01J 3/46* (2006.01)
   *G01J 3/52* (2006.01)
   *H04N 9/04* (2006.01)
   *A61C 13/08* (2006.01)
   *A61C 13/00* (2006.01)

(52) U.S. Cl.
   CPC ............. *G01J 3/508* (2013.01); *G01J 3/524* (2013.01); *H04N 1/60* (2013.01); *H04N 9/045* (2013.01); *H04N 17/002* (2013.01); *A61C 13/0004* (2013.01); *A61C 13/082* (2013.01); *G01J 2003/466* (2013.01); *G06K 2209/055* (2013.01)

(58) Field of Classification Search
   CPC .... G01J 3/462; G01J 3/524; G01J 3/50; G01J 3/463; G01J 3/508; G01J 2003/466; A61C 13/0004; A61C 13/082
   See application file for complete search history.

(56) References Cited

U.S. PATENT DOCUMENTS

| | | | | |
|---|---|---|---|---|
| 2008/0144143 | A1* | 6/2008 | Solechnik | G01J 3/46 358/520 |
| 2008/0160485 | A1* | 7/2008 | Touchstone | A61C 13/0004 433/215 |

OTHER PUBLICATIONS

M.N. Carney, W.M. Johnston, Appearance Differences Between Lots and Brands of Similar Shade Designations of Dental Composite Resins, Journal of Esthetic and Restorative Dentistry 2016, 9 pages.

M.N. Carney, W.M. Johnston, The development of a novel shade selection program for fixed shade translucent dental materials, Journal of Dentistry 62, 2017, 81-84. http://dx.doi.org/10.1016/j.jdent.2017.05.002.

Shigemi, et al., Using a computer color-matching system in color reproduction of porcelain restoration. Part 3: A newly developed spectrophotometer designed for clinical application. The international Journal of Prosthodontics 1994, 7 pages.

Shigemi, et al., Using a computer color-matching system in color reproduction of porcelain restoration. Part 2: Color reproduction of stratiform-layered porcelain samples. The international Journal of Prosthodontics 1993, 7 pages.

Shigemi, et al., Using a computer color-matching system in color reproduction of porcelain restoration. Part 1: Application of CCM to the opaque layer. The international Journal of Prosthodontics 1992, 9 pages.

Shigemi, et al., Developing a custom dental porcelain shade system for computer color matching, Journal of Dentistry 2013, e3-e10.

Amidror I. Scattered data interpolation methods for electronic imaging systems: a survey. Journal of Electronic Imaging 2002; 11(2):157-76.

Bolt RA, Bosch JJ, Coops JC. Influence of window size in small-window colour measurement, particularly of teeth. Phys Med Biol 1994; 39(7):1133-42.

Chartrand TL, Bargh JA. The chameleon effect: the perception-behavior link and social interaction. J Pers Soc Psychol 1999; 76(6):893-910.

Chu SJ, Trushkowsky RD, Paravina RD. Dental color matching instruments and systems. Review of clinical and research aspects. J Dent 2010; 38 Suppl 2:e2-16.

Crisp S, Abel G, Wilson AD. The quantitative measurement of the opacity of aesthetic dental filling materials. Journal of Dental Research 1979; 58(6):1585-96.

da Costa J, Fox P, Ferracane J. Comparison of various resin composite shades and layering technique with a shade guide. J Esthet Restor Dent 2010; 22(2):114-24.

Davis BK, Johnston WM, Saba RF. Kubelka-Munk reflectance theory applied to porcelain veneer systems using a colorimeter. Int J Prosthodont 1994; 7(3):227-33. Abstract.

Douglas RD, Brewer JD. Acceptability of shade differences in metal ceramic crowns. J Prosthet Dent 1998; 79(3):254-60.

Douglas RD. Precision of in vivo colorimetric assessments of teeth. The Journal of Prosthetic Dentistry 1997; 77(5):464-70.

Fach C, Sharpe LT. Assimilative hue shifts in color gratings depend on bar width. Percept Psychophys 1986; 40(6):412-8.

Ghinea R, Pérez MM, Herrera LJ, Rivas MJ, Yebra A, Paravina RD. Color difference thresholds in dental ceramics. Journal of dentistry 2010; 38:e57-e64.

Hall NR, Kafalias MC. Composite colour matching: the development and evaluation of a restorative colour matching system. Aust Prosthodont J 1991; 5:47-52. Abstract.

Helson H. Studies of anomalous contrast and assimilation. J Opt Soc Am 1963; 53:179-84.

Hong G, Luo MR, Rhodes PA. A study of digital camera colorimetric characterization based on polynomial modeling. Color Research & Application 2001; 26(1):76-84.

Hunter RS. The Measurement of Appearance. New York: John Wley and Sons; 1975. p. 199-200.

Jivanescu A, Marcauteanu C, Pop D, Goguta L, Bratu D. Conventional Versus Spectrophotometric Shade Taking for the Upper Central Incisor: A Clinical Comparative Study.

Johnston WM, Ma T, Kienle BH. Translucency parameter of colorants for maxillofacial prostheses. Int J Prosthodont 1995; 8(1):79-86.

Johnston WM, Reisbick MH. Color and translucency changes during and after curing of esthetic restorative materials. Dental Materials 1997; 13(2):89-97.

Johnston WM. Review of Translucency Determinations and Applications to Dental Materials. Journal of Esthetic and Restorative Dentistry 2014; 26(4):217-23.

Judd DB, Harrison W, Sweo B, Hickson E, Eickhoff A, Shaw M, et al. Optical specification of light-scattering materials. J Res Nat Bur Stand 1937; 19:287-317.

Khurana R, Tredwin CJ, Weisbloom M, Moles DR. A clinical evaluation of the individual repeatability of three commercially available colour measuring devices. Br Dent J 2007; 203(12):675-80.

Kielbassa AM, Beheim-Schwarzbach NJ, Neumann K, Nat R, Zantner C. In vitro comparison of visual and computer-aided pre- and post-tooth shade determination using various home bleaching procedures. J Prosthet Dent 2009; 101(2):92-100.

Kim-Pusateri S, Brewer JD, Davis EL, Wee AG. Reliability and accuracy of four dental shade-matching devices. J Prosthet Dent 2009; 101(3):193-9.

Kubelka P, Munk F. Ein beitrag zur optik der farbanstriche. Zeitschrift fr Technische Physik 1931; 12:593-601. English abstract.

Kubelka P. New Contributions to the Optics of Intensely Light-Scattering Materials. Part I. J Opt Soc Am 1948; 38(5):448-48.

Kürklü D, Azer SS, Yilmaz B, Johnston WM. Porcelain thickness and cement shade effects on the colour and translucency of porcelain veneering materials. Journal of dentistry 2013; 41(11):1043-50.

Lagouvardos PE, Fougia AG, Diamantopoulou SA, Polyzois GL. Repeatability and interdevice reliability of two portable color selection devices in matching and measuring tooth color. J Prosthet Dent 2009;101(1):40-5.

Lindsey DT, Wee AG. Perceptibility and acceptability of CIELAB color differences in computer-simulated teeth. J Dent 2007; 35(7):593-9.

Lopez F ea. Fast surface grading using color statistics in the CIELab space. Conference on Patern Recognition and Image Analysis. Iberian; 2005, 8 pages.

Luo MR, Cui G, Rigg B. The development of the CIE 2000 colour-difference formula: CIEDE2000. Color Research & Application 2001; 26(5):340-50.

McCamy CS. Colors of some small figures on colored grounds. Color Research & Application 2003; 28(4):242-50.

(56) References Cited

OTHER PUBLICATIONS

Mikhail SS, Azer SS, Johnston WM. Accuracy of Kubelka—Munk reflectance theory for dental resin composite material. Dental Materials; 28(7):729-35.

Mikhail SS, Schricker SR, Azer SS, Brantley WA, Johnston WM. Optical characteristics of contemporary dental composite resin materials. Journal of dentistry; 41(9):771-78.

Miyagawa Y, Powers J, O'brien W. Optical properties of direct restorative materials. Journal of Dental Research 1981; 60(5):890-94.

O'brien W, Groh C, Boenke K. A new, small-color-difference equation for dental shades. Journal of Dental Research 1990; 69(11):1762-64.

O'Brien WJ, Johnston WM, Fanian F. Double-layer Color Effects in Porcelain Systems. Journal of Dental Research 1985; 64(6):940-43.

Paravina RD, Westland S, Imai FH, Kimura M, Powers JM. Evaluation of blending effect of composites related to restoration size. Dental materials: official publication of the Academy of Dental Materials 2006; 22(4):299-307.

Paravina RD, Westland S, Kimura M, Powers JM, Imai FH. Color interaction of dental materials: Blending effect of layered composites. Dental materials: official publication of the Academy of Dental Materials 2006; 22(10):903-08.

Paul SJ, Peter A, Rodoni L, Pietrobon N. Conventional visual vs spectrophotometric shade taking for porcelain-fused-to-metal crowns: a clinical comparison. Int J Periodontics Restorative Dent 2004; 24(3):222-31.

Pridmore RW. Bezold—Brucke effect exists in related and unrelated colors and resembles the Abney effect. Color Research & Application 2004; 29(3):241-46.

Ragain JC, Johnston WM. Color acceptance of direct dental restorative materials by human observers. Color Research & Application 2000; 25(4):278-85.

Sawyer RH. Hiding power and opacity. Symposium on Color; 1941: ASTM International; 1941. p. 23.

Seghi RR, Johnston WM, O'Brien WJ. Performance assessment of colorimetric devices on dental porcelains. J Dent Res 1989; 68(12):1755-9.

Sharma G, Wu W, Dalal EN. The CIEDE2000 color-difference formula: Implementation notes, supplementary test data, and mathematical observations. Color Research & Application 2005; 30(1):21-30.

Shinoda H, Ikeda M. Color assimilation on grating affected by its apparent stripe width. Color Research & Application 2004; 29(3):187-95.

Spitzer D, Bosch JT. The absorption and scattering of light in bovine and human dental enamel. Calcif Tissue Res 1975; 17(2):129-37.

Swift EJ, Jr., Hammel SA, Lund PS. Colorimetric evaluation of vita shade resin composites. Int J Prosthodont 1994; 7(4):356-61. Abstract.

Tanaka A, Nakajima M, Seki N, Foxton RM, Tagami J. The effect of tooth age on colour adjustment potential of resin composite restorations. J Dent 2015; 43(2):253-60.

Walker J. Brightness enhancement and the Talbot level in stationary gratings. Attention, Perception, & Psychophysics 1978; 23(4):356-59.

Wee AG, Lindsey DT, Kuo S, Johnston WM. Color accuracy of commercial digital cameras for use in dentistry. Dent Mater 2006; 22(6):553-9.

Weder S. A Custom Shade Guide System for Composite Resins. Journal of Esthetic and Restorative Dentistry 1990; 2(1):10-12.

Yu B, Lee Y-K. Influence of color parameters of resin composites on their translucency. Dental Materials 2008; 24(9):1236-42.

\* cited by examiner

IMAGE COLOR DATA NORMALIZATION AND COLOR MATCHING SYSTEM FOR TRANSLUCENT MATERIAL

CROSS-REFERENCE TO RELATED APPLICATION

This application claims priority to U.S. Provisional Patent Application No. 62/332,783, entitled, "Novel Color Matching System for Translucent Dental Material," filed May 6, 2016, the which is incorporated herein by reference in its entirety.

STATEMENT OF GOVERNMENT SUPPORT

This invention was made with government support under T32 DE014320 awarded by the National Institutes of Health. The government has certain rights in the invention.

BACKGROUND OF THE DISCLOSURE

There are several types of devices that are currently used in clinical settings for shade matching in dentistry. Spectrophotometers are considered to be amongst the most accurate and functional devices for these purposes. A spectrophotometer includes an optical radiation source, a light dispersing source, an optical measuring system, a detector, and a means of converting light to a signal for analysis and manipulation that is useful to the investigator. These devices measure an amount of light energy that is reflected from a specific object along the spectrum of visible light in 1-25 nm intervals. In the dental setting, the clinically obtained measurements are often compared to a shade guide to select a matching color of dental material that most closely matches a patient's natural tooth color.

Colorimeters are another device used for color measurement and shade matching. The data acquired by a colorimeter is often very precise because contact is made with the actual tooth. However, colorimeters do not measure spectral reflectance and are less accurate than spectrophotometers. Conventional colorimeters that utilize CIE recommended geometries for reflection measurements are generally not best for use of measuring objects with a translucent nature due to inaccuracies caused by the optical phenomenon of edge effects.

Yet another imaging device that is often used in clinical settings is the digital camera. Digital cameras are often used for this purpose because they are relatively inexpensive. Information obtained from a digital camera is generally input in a Red, Green and Blue (RGB) color space, but the RGB information is device dependent. As such, the RGB information must be adjusted and calibrated in order to utilize the color information extracted from a digital image. For color analysis involving digital camera sources, conversion equations from the RGB color space system to the CIE L*a*b* (CIELAB) color space are necessary. However, because RGB data obtained from a digital camera is device dependent, complex calibration models are needed in order to render with optimal accuracy.

For color analysis involving digital camera sources, conversion equations from RGB color space system to the CIELAB color space system may utilize a matrix that converts RGB color data to XYZ tristimulus values as follows:

$$\begin{bmatrix} X \\ Y \\ Z \end{bmatrix} = \begin{bmatrix} 0.412453 & 0.357580 & 0.180423 \\ 0.212671 & 0.715160 & 0.072169 \\ 0.019334 & 0.119193 & 0.950227 \end{bmatrix} \times \begin{bmatrix} R \\ G \\ B \end{bmatrix}$$

Prior work has evaluated four calibration models with three different digital cameras using the cameras' RGB values compared to the CIELAB values as a reference standard for accuracy measurements defined by $\Delta E$. A second order polynomial regression (PRM2), a second order polynomial regression with eleven terms (PRM2-11), a third order polynomial regression (PRM3), and a model based on tetrahedral interpolation (TI) technique were all compared for accuracy. The models that were analyzed are as follows:

Second order polynomial regression (PRM2)

$$L^* = l_0 + l_1 R + l_2 G + l_3 B + l_4 RG + l_5 RB + l_6 GB + l_7 R^2 + l_8 G^2 + l_9 B^2$$

Second order polynomial regression with eleven terms (PRM2-11)

$$L^* = l_0 + l_1 R + l_2 G + l_3 B + l_4 RG + l_5 RB + l_6 GB + l_7 R^2 + l_8 G^2 + l_9 B^2 + l_{10} RGB$$

Third order polynomial regression (PRM3)

$$L^* = l_0 + l_1 R + l_2 G + l_3 B + l_4 RG + l_5 RB + l_6 GB + l_7 R^2 + l_8 G^2 + l_9 B^2 + l_{10} RGB + l_{11} R^3 + l_{12} G^3 + l_{13} B^3 + l_{14} R^2 G + l_{15} R^2 B + l_{16} G^2 R + l_{17} G^2 B + l_{18} B^2 R + l_{10} B^2 G$$

In general, accuracy is improved by increasing the terms and raising the order of the regression model with proper terms being more important than increase of terms. In addition, using TI generally provided better results than using PRM2-11, and the results obtained using PRM3 were similar when compared to the results obtained using TI. Three out of 12 calibration/camera pairs were found to be below the $\Delta E$ acceptability limit of 2.1 lending to the idea that inexpensive digital cameras used in combination with specific calibration methods have potential in the clinical processes involving color replication.

SUMMARY OF THE DISCLOSURE

A method and system for color matching of translucent materials and for normalization, standardization, and accuracy validation of color image data as well as a mathematical model to quantify blending or color adjustment potential are proposed.

In accordance with an aspect of the disclosure, a method for calibrating an imaging device is disclosed that includes obtaining standardized image data associated with a specimen; acquiring images of the specimen using the imaging device; extracting Red, Green and Blue (RGB) values from the images; developing a regression model to convert the RGB values to the CIELAB standard color space utilizing spectral radiance, spectral reflectivity, absorption, scattering, CIELAB color coordinates, or any units of the CIE color space while normalizing for accuracy.

In accordance with another aspect of the disclosure, a method for color matching of translucent materials is disclosed that includes acquiring one or more images of a region of interest using a digital imaging device; applying regression modeling to convert an acquired Red, Green and Blue (RGB) color space value to a value that has been adjusted for accuracy and converted to spectral radiance, spectral reflectivity, absorption, scattering, CIELAB color coordinates, CIELAB XYZ tristimulus values, or any units of the CIE color space; comparing these values to master shade specimens contained in a database; selecting one of the master shade specimens that best matches the normalized value by having a smallest color difference relative to the normalized RGB value; and presenting an indication of the selected one of the master shade specimens to a user in a user interface.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION OF THE DISCLOSURE

Unless defined otherwise, all technical and scientific terms used herein have the same meaning as commonly understood by one of ordinary skill in the art to which the disclosure belongs. Any methods and materials similar or equivalent to those described herein can be used in the practice or testing of the present disclosure.

Overview

In an aspect of the present disclosure, example methods for calibrating RGB data acquired from a digital camera are described so the data can be used for, e.g., color matching of translucent materials. The normalization of the RGB data may be used for other purposes, but is described herein with reference to clinical settings to perform matching of a composite resin to tooth shade. Typically this matching is a subjective process performed by a clinician using a shade guide. In another aspect of the present disclosure, a method and system for objectively selecting a best match of a composite resin to a natural dentition is described. The methods and systems can be expanded to include the matching of any translucent material to the color of a region of translucent material of interest.

Calibration of RGB Data

Figure 1:
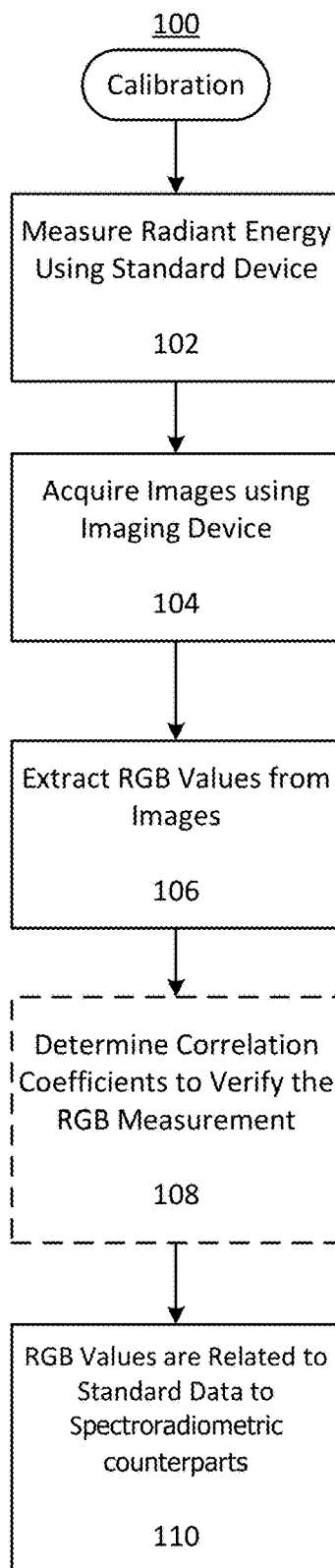
FIG. 1 illustrates an example operational flow in accordance with the present disclosure to calibrate RGB data for optimal accuracy generated by an imaging device.

FIG. 1 illustrates an example operational flow in accordance with the present disclosure to calibrate RGB data generated by an imaging device. At 102, radiant energy of master specimens is measured using a standard device, such as a spectroradiometer. In one example process, a plurality of master shade specimens was characterized by measuring the radiant energy using, e.g., a spectroradiometer (e.g., PR 705; Photo Research Inc., Chatsworth, Calif.) and a Xenon arc lamp (e.g., 300 W; Oriel Instruments, Stratford, Conn.), with a connected fiber optic light cable. The spectroradiometer and optic light cable may be placed inferiorly to the horizontal plane at a 45-degree angle in order to result in a 0-degree observation and a 45-degree illumination optical configuration for measurement. A measurement of radiant energy was produced for this central point on the standard from 380 nm to 780 nm in increments of 2 nm (e.g., Spectrawin 2.0; Photo Research Inc.). The central ninth of each shade guide tab was measured and the radiant energy data was converted to spectral reflectance and then to CIE XYZ values. The spectroradiometric data can be used to match acquired RGB data with a particular shade after performing the operation flow 100.

At 104, digital images are taken of the same points on the master shade specimens using an imaging device such as a digital camera, smartphone, tablet, or other handheld imaging device. For example, the images may be taken using a Canon Rebel T3i with an aperture setting of F22, an ISO of 200, a shutter speed of 1/200, the focal length set to 0.39, and the white balance set to a standard gray card. A Canon Ring Lite MR-14EX flash may be used with a 1/4 flash output.

To verify the above settings, photographs of black, white, and gray opaque standards were taken under different ambient light conditions as well as in different surrounding environments. Ambient light conditions included D65 daylight, cool white fluorescent, and no ambient light underneath the hood. Surrounding environment conditions included the opaque standards on a white and black backing and surround. Aperture, flash output, white balance, shutter speed, and any other controllable settings were adjusted until minimization of these various external environments occurred. The ability to minimize these variables was a necessity for clinical relevance to the model.

In the example above (at 104), in order to analytically determine whether or not minimization of the environmental factors had occurred, image data was analyzed using image J to extract RGB values from the images. These values were analyzed systematically at precise positions on the images of the standards and were statistically analyzed to ensure that the RGB values were similar under all the various illumination conditions with different surrounds and backings. In order to compare color measurements taken from the camera and color measurements taken from the spectroradiometer, measurements of the radiant energy of the opaque standards were also taken using the spectroradiometer as described previously. The same position that was measured on the opaque standard using image J was measured on the spectroradiometer. The radiant energy data was immediately converted to spectral reflectance.

At 106, RGB values are extracted from the images of, e.g., the central ninth of each of the shade tabs. Two or more measurements of RGB data from the images for each of shade tabs may be taken using the central ninth of each shade tab. The multiple measurements for these shade tabs may be averaged for the shade tabs that were measured more than once.

At 108, correlation coefficients may be determined to verify the method of RGB measurement of the image data. For example, intraclass correlation coefficients for shade tabs that were measured multiple times and for shade tabs that were duplicated within the shade guides may be determined using, e.g., a SAS GLM procedure (PROC GLM, SAS® Proprietary Software 9.3, SAS Institute Inc., Cary, N.C., USA). This procedure may be performed in order to determine the reliability of the RGB determination methodology used and in order to analyze the variability in same shade designations within the master shade guides. The means of the RGB values may be determined for each shade represented in the two shade guides used.

The means may then be used for the regression model determination. At 110, the RGB data is related to the spectroradiometric data such that is calibrated to the equivalent spectroradiometric measurements. For example, a linear regression model without y-intercept relating RGB values to XYZ values may be generated using linear regression without intercept programming. This regression may utilize all of the thirty six distinct shades included in the shade guides. An "R" value may be determined in order to indicate a level of correlation between the two systems of color description. Using the regression model, the RGB values are then converted to Commission Internationale d'Eclairage XYZ tristimulus values with D65 illumination and a 2-degree observer or to spectral radiance, spectral reflectivity, absorption, scattering, CIELAB color coordinates, CIELAB XYZ tristimulus values, or any units of the CIE color space. The spectral reflectance data from the same specimens was also converted to spectral radiance, spectral reflectivity, absorption, scattering, CIELAB color coordinates, CIELAB XYZ tristimulus values, or any units of the CIE color space. This regression allows digital images to provide color information for a wide range of tooth color shades that can be used to accurately translate color information.

Once the RGB values are converted to XYZ values, they can be converted to the L*, a*, b* values using the following relationships:

$$L^* = 116 f(Y/Y_n) - 16$$

$$a^* = 500 \left[ f\left(\frac{X}{X_n}\right) - f\left(\frac{Y}{Y_n}\right) \right]$$

$$b^* = 200 \left[ f\left(\frac{Y}{Y_n}\right) - f\left(\frac{Z}{Z_n}\right) \right]$$

where $f(I) = I^{1/3}$ for $I > 0.008856$ and for all others $$f(I) = 7.787 + \frac{16}{116}$$

with X, Y, Z, and $X_n$, $Y_n$, and $Z_n$ representing the sample CIE tristimulus values and the standard tristimulus values respectively.

Using these methods to calculate these coordinates, L* represents lightness ranging from 0-100, a* represents red-green chromaticity with a positive a* indicating tendency toward red and a negative a* indicating a tendency toward green, and b* represents yellow-blue chromaticity with a positive b* indicating a tendency toward yellow and a negative b* indicating a tendency toward blue. CIE hue and chroma may be calculated using the a* and b* coordinates by the following equations:

$$h_{ab} = a \tan 2(b^*, a^*)$$

$$c_{ab} = \sqrt{a^{*2} + b^{*2}}$$

In order to quantify the color difference that is perceived between samples, the CIELAB color difference formula (CIEDE2000) may be used. This color difference formula has proven especially useful in dentistry for purposes of measuring the accuracy and the precision of color measuring instruments, assessing the effects of processing and aging on color of dental materials, and calculating acceptability, perceptibility, and translucency parameters. The $\Delta E_{ab}$ color difference formula provides this valuable information as follows:

$$\Delta E_{ab} = \sqrt{(\Delta L^*)^2 + (\Delta a^*)^2 + (\Delta b^*)^2}$$

where $\Delta L^*$, $\Delta a^*$, and $\Delta b^*$ represent the change in each of the tristimulus values L*, and b*. The color difference as a result of change in hue is found using the following equation:

$$\Delta H^*_{ab} = \sqrt{(\Delta E_{ab})^2 - (\Delta L^*)^2 - (\Delta C^*_b)^2}$$

where $\Delta C^*_{ab}$ represents the chroma difference for two color.

A more modern color difference formula ($\Delta E'$ or CIEDE2000) with five correction provisions that incorporate the original hue and chroma ideas from Munsell as well as a correction function that compensates for the problematic area in the blue region is suggested as follows:

$$\Delta E' = \left[ \left(\frac{\Delta L'}{K_L S_L}\right)^2 + \left(\frac{\Delta C'}{K_C S_C}\right)^2 + \left(\frac{\Delta H'}{K_H S_H}\right)^2 + R_T \left(\frac{\Delta C'}{K_C S_C}\right)\left(\frac{\Delta H'}{K_H S_H}\right) \right]^{\frac{1}{2}}$$

where $\Delta L'$, $\Delta C'$, and $\Delta H'$ represent the difference in lightness, chroma, and hue respectively for two samples and $R_T$ represents a rotation function that compensates for the relationship between the hue and chroma differences that can be problematic in the blue area. $K_L$, $K_C$, and $K_H$ represent factors correcting for experimental conditions that are valued at 1. $S_L$, $S_C$, and $S_H$ are terms that correct for discrepancy between the location of the L', a', b' coordinates for each sample within the pair being analyzed.

A regression was performed relating RGB values to spectral radiance, spectral reflectivity, absorption, scattering, CIELAB color coordinates, CIELAB XYZ tristimulus values, or any units of the CIE color space. A high R value indicated a good correlation between the two systems of color description. Using this regression model, the RGB values were then converted to spectral radiance, spectral reflectivity, absorption, scattering, CIELAB color coordinates, CIELAB XYZ tristimulus values, or any units of the CIE color space using D65 illumination and a two degree observer. The spectral reflectance data from the same specimens was converted accordingly.

In order to optimize the digital camera calibration parameters for color accuracy of translucent tooth colored specimens, the master shade guides were characterized by measuring the radiant energy of each shade tab using the spectroradiometer with the configuration previously described. The central ninth of each shade guide tab was measured. The radiant energy data was converted to spectral reflectance and then to X, Y and Z values, and therefore to the standard CIE color space format. Although the above describes conversion to X, Y and Z values and then to CIELAB values, it is noted that the conversion may be to spectral radiance, spectral reflectivity, absorption, scattering, CIELAB color coordinates, CIELAB XYZ tristimulus values, or any units of the CIE color space. The same points on the shade tab specimens were photographed under different ambient light conditions and the RGB values were analyzed and extracted with Image J in the same manner as previously described. The regression model was generated relating the RGB data from the camera to the spectroradiometric counterpart. This further refined the camera settings to accurately record a wide range of tooth color shades.

Table 1 contains summarized data from the shade tabs contained in the master shade guides.

TABLE 1

Summary of Frequency, Mean, and Range of Shade Tabs from, e.g., VITA Linearguide 3D Master and the VITA Bleached Guide 3D Master Shade Guides

| Variable | N | Mean | Minimum | Maximum |
| --- | --- | --- | --- | --- |
| XCap | 50 | 40.52 | 26.73 | 58.43 |
| YCap | 50 | 42.21 | 26.91 | 61.60 |
| ZCap | 50 | 31.95 | 14.08 | 61.60 |
| L* | 50 | 70.50 | 58.89 | 82.70 |
| a* | 50 | 1.54 | −1.06 | 5.23 |
| b* | 50 | 18.33 | 4.75 | 30.05 |

Table 2 contains the intraclass correlation coefficients for multiple RGB measurements of the same shade tab.

TABLE 2

Intraclass Correlation Coefficients for Multiple RGB Measurements of the Same Shade Tab.

| | Shrout-Fleiss Reliability Single Score |
| --- | --- |
| R | 0.94 |
| G | 0.97 |
| B | 0.98 |

Table 3 contains the intraclass correlation coefficients for multiple shade tabs with the same shade designation.

TABLE 3

Intraclass Correlation Coefficients for Multiple Shade Tabs with the Same Shade Designations

| | Shrout-Fleiss Reliability Single Score |
| --- | --- |
| R | 0.84 |
| G | 0.97 |
| B | 0.97 |

Figure 2:
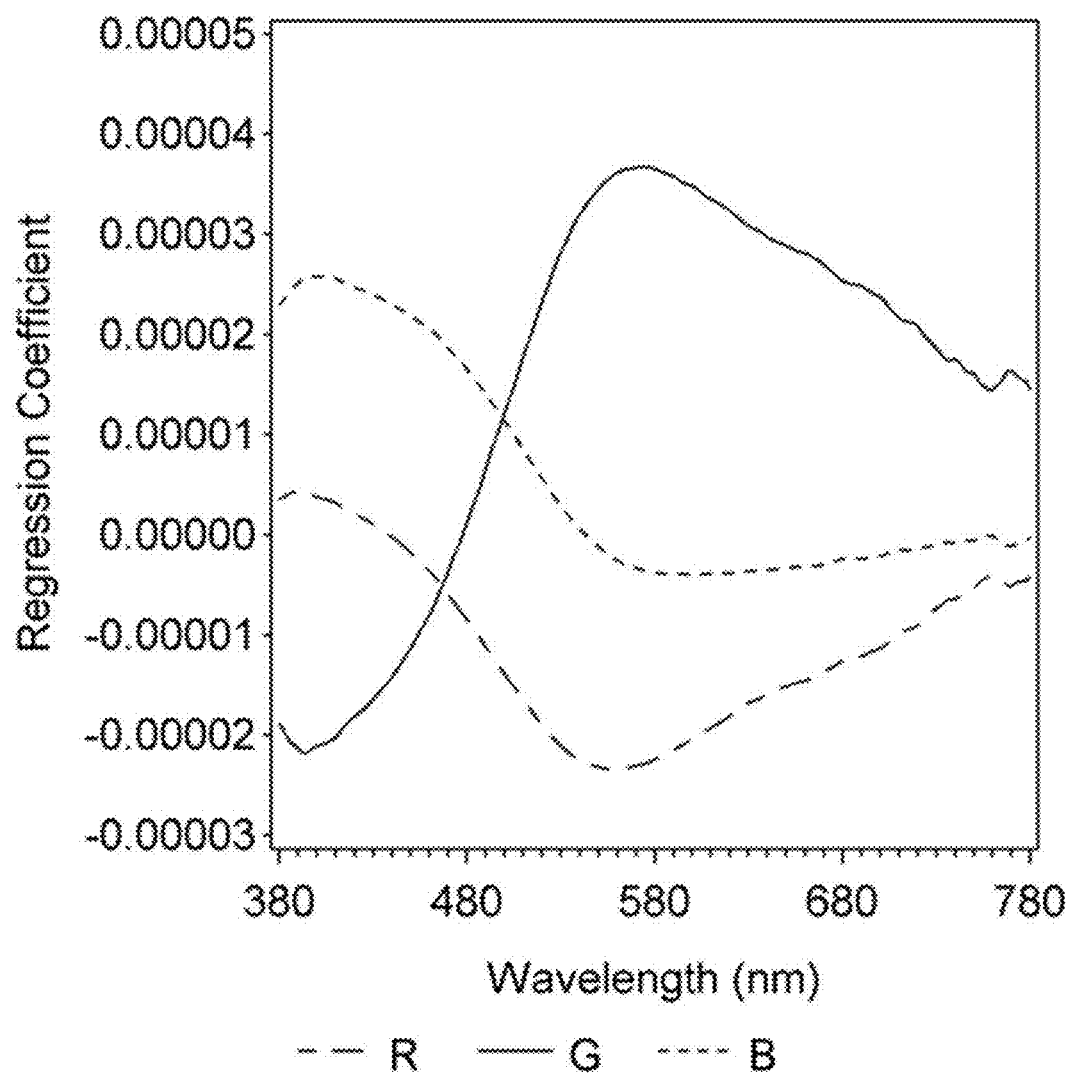
FIG. 2 illustrates the relationship between the regression coefficients for the RGB color space with wavelength in the visible spectrum.
Figure 3:
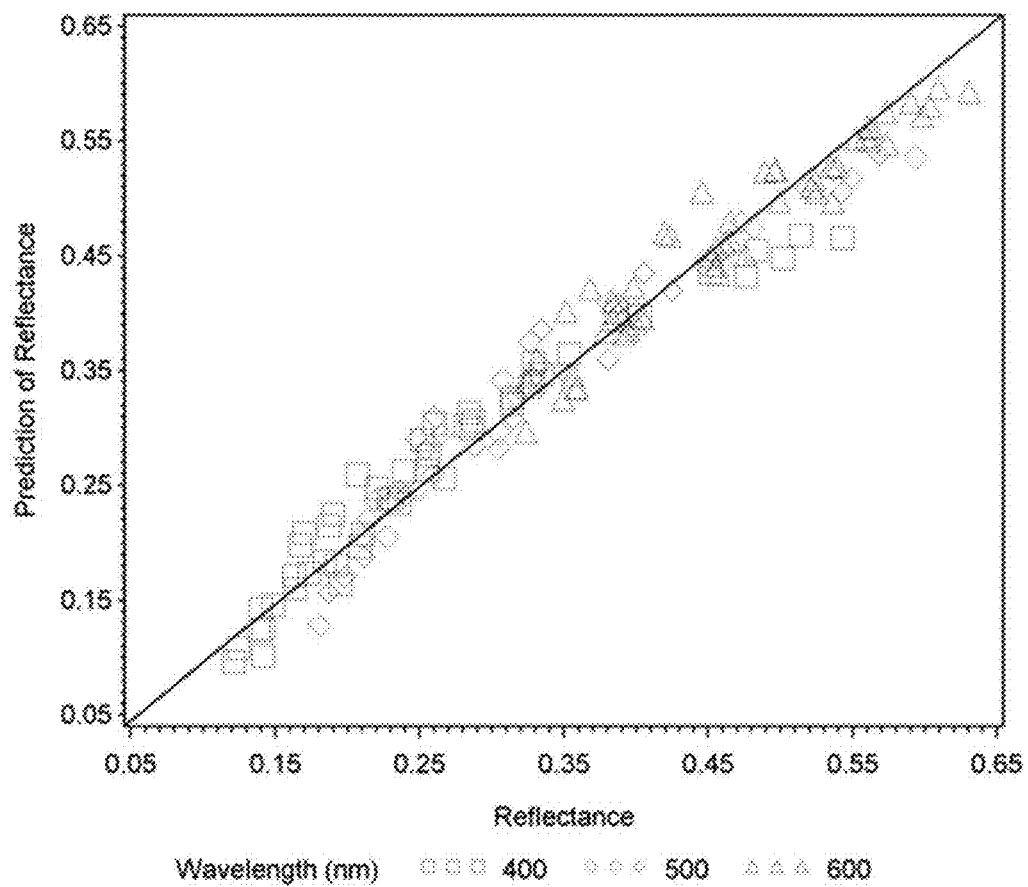
FIG. 3 illustrates predictions of reflectance from RGB color space information using the determined regression model at wavelengths 400 nm, 500 nm and 600 nm.
Figure 4:
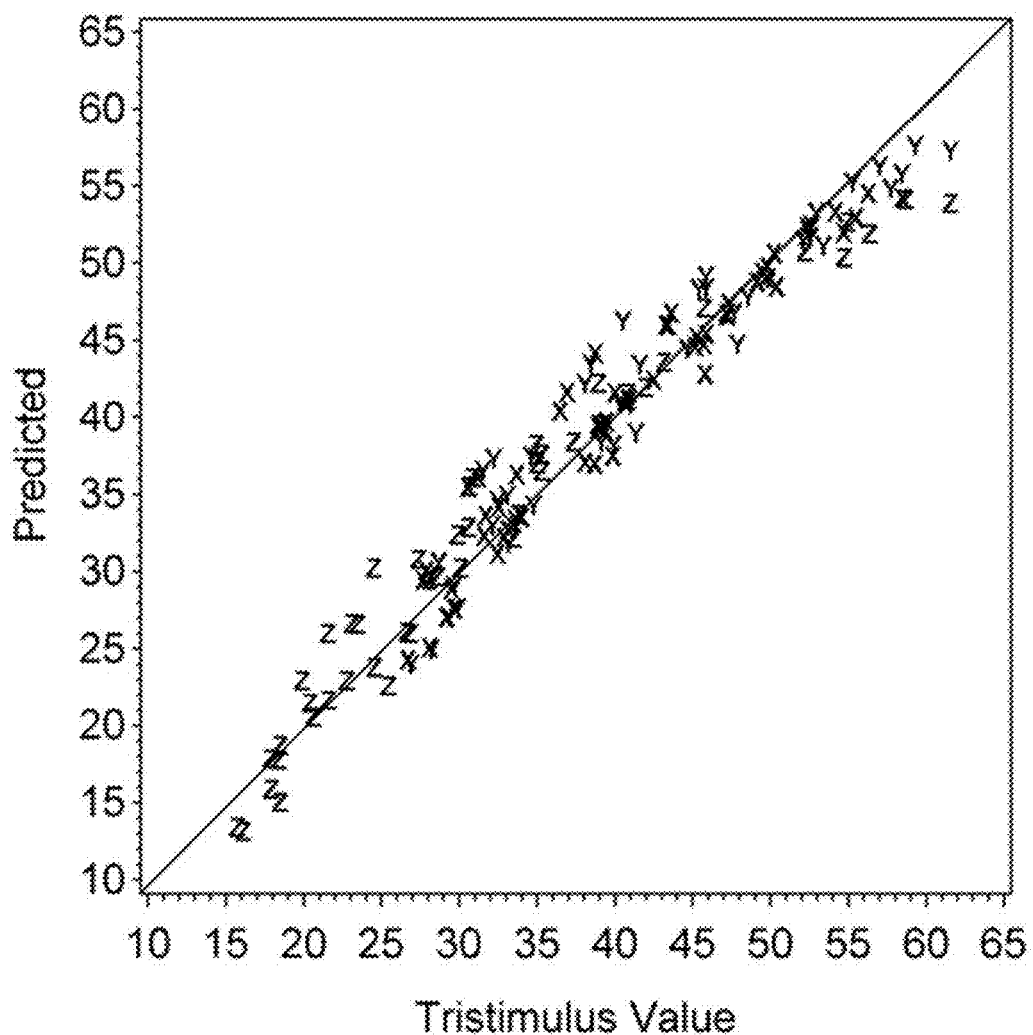
FIG. 4 illustrates the predictions of XYZ from the RGB color space using the determined regression model.

FIG. 2 demonstrates how the slopes of the regression which are the regression coefficients for RGB vary with wavelength in the visible spectrum. Predictions of reflectance from RGB using the determined regression model at wavelengths 400 nm, 500 nm, and 600 nm can be seen in FIG. 3. FIG. 4 shows the predictions of XYZ from RGB using the determined regression model.

Table 4 displays the R-squared values for the regressions from RGB to XYZ and to absolute reflectance at wavelengths 400 nm, 500 nm, and 600 nm.

TABLE 4

Regression R-Squared Values

| Dependent Variable | R-Squared |
| --- | --- |
| X-Cap | 1.00 |
| Y-Cap | 1.00 |
| Z-Cap | 0.99 |
| Absolute Reflectance 400 nm | 0.96 |
| Absolute Reflectance 500 nm | 0.97 |
| Absolute Reflectance 600 nm | 0.95 |

Table 5 displays basic statistics for the RGB data with the lightness number from the shade guide (L3D).

TABLE 5

Simple Statistics for RGB Values with Lightness Number From Shade Guide (L3D)

| Variable | N | Mean | Std Dev | Min | Max |
| --- | --- | --- | --- | --- | --- |
| B | 36 | 43766 | 6933 | 32230 | 57330 |
| G | 36 | 51112 | 4143 | 43564 | 58475 |
| R | 36 | 55540 | 2137 | 50377 | 59179 |
| L3D | 36 | 2.74 | 1.49 | 0 | 5.00 |

Table 6 displays the correlation coefficients squared for L3D related to RGB values and the P-values from a test of the hypothesis of no correlation.

TABLE 6

Pearson Correlation Coefficients Squared for RGB Related to L3D and the P-Values from a Test of the Hypothesis of No Correlation

| | R | G | B |
| --- | --- | --- | --- |
| 3D | 0.85 [P < .0001] | 0.97 [P < .0001] | 0.94 [P < .0001] |

The regression data from RGB to CIELAB standard color space normalized to the spectroradiometer via spectral radiance, spectral reflectivity, absorption, scattering, CIELAB color coordinates, CIELAB XYZ tristimulus values, or any units of the CIE color space. is the foundation for translation of the theoretical color matching to a clinical color matching system that uses digital imaging. The regression model allows for a color range that is especially relevant over all tooth shades that can be represented in the master shade guides. Expanding on the above, the regression model can be used for any color of any translucent material. The high R squared values for predictions of reflectance indicate that the regression is a good fit and explains a high proportion of the variance in reflectance. The charts indicating RGB values for each shade in the shade guide provide a summary of this data for the entire shade guide. The high intraclass correlation coefficients for multiple measurements of the same shade tab indicate a reliable system of measurement and extraction of RGB image data. The intraclass correlation coefficients for multiple shade tabs with the same shade designations indicate high reliability and little variability for G and B measurements while measurements of R had the most variability. In addition, the high correlation coefficients between the RGB values each with the L3D value indicate a statistically significant relationship between the RGB values and the lightness or value number indicated on the shade guide.

Color Matching

Figure 5:
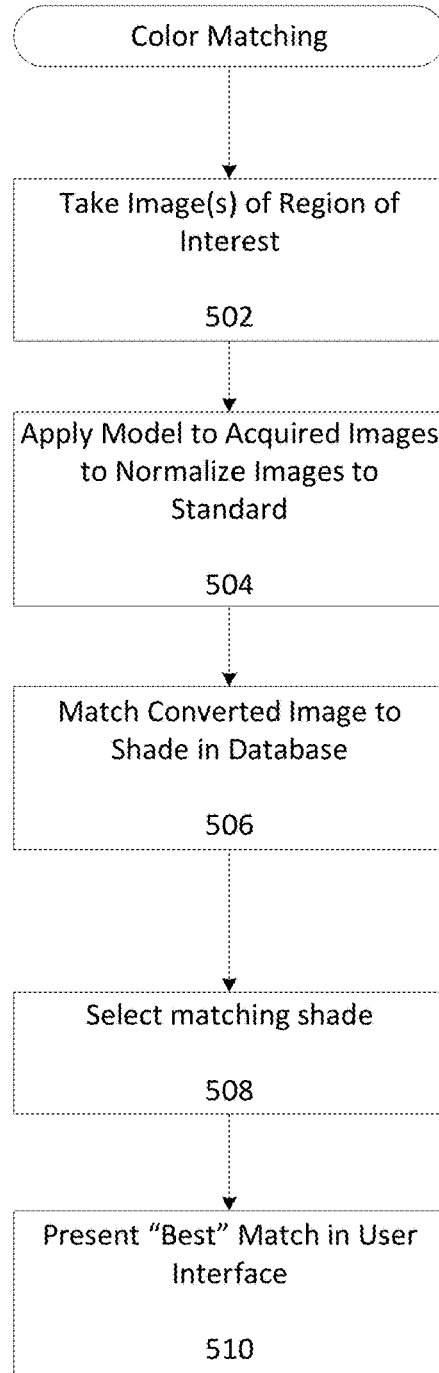
FIG. 5 illustrates an example operational flow for using digital imaging for shade matching.
Figure 6:
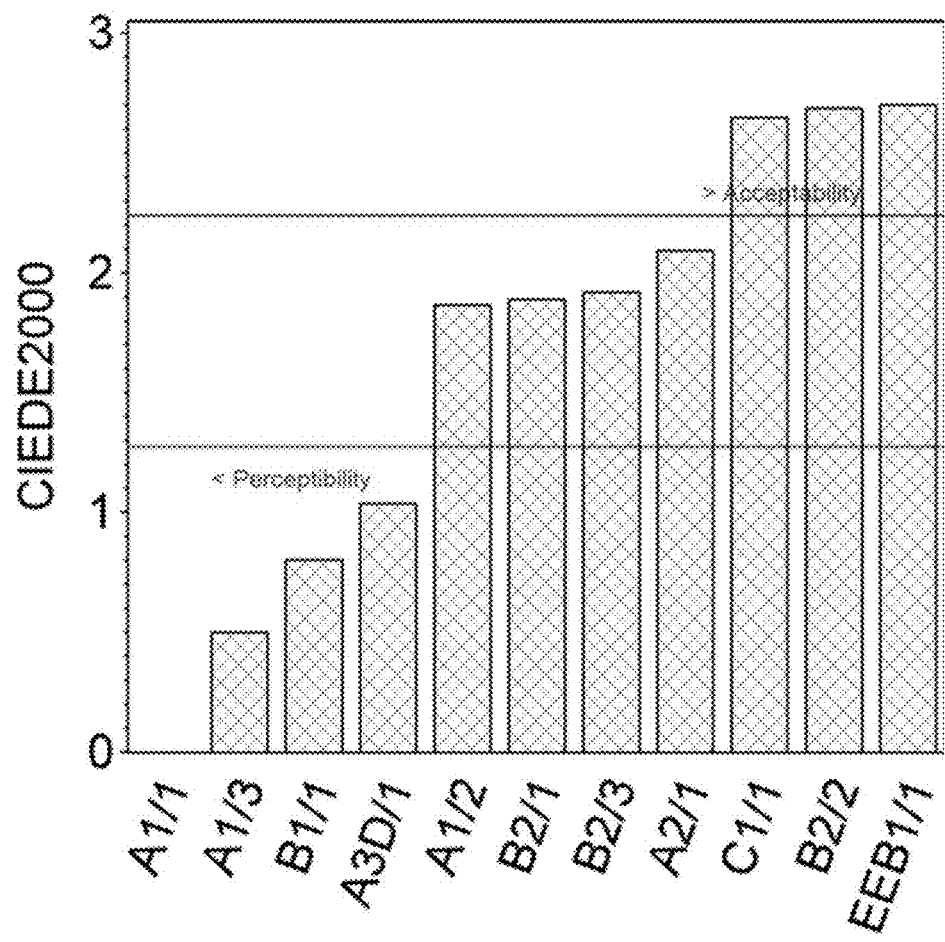
FIG. 6 illustrates CIEDE2000 color differences between selected shades and the target shade with perceptibility and acceptability thresholds using the same Herculite Ultra backing shade (B) and target shade (T) in accordance with a direct method using reflectance data.

In another aspect, the present disclosure includes methods and systems to select a restorative material that best matches the natural dentition using a shade selection program. Presently, translation of visual color to a selection of a best matching restorative material is a complicated process that can produce a high amount of inter-observer variability and lack of objectivity. The present disclosure utilizes digital imaging, regression modeling, and Kubelka-Munk Theory of Reflectance to aid in optimum and efficient shade matching. Thus, with reference to FIG. 5, at 502, one or more images of a region of interest may be taken using a digital imaging device, such as a digital camera, smartphone, tablet or other handheld device. At 504, the shade selection program may apply the regression modeling described above to convert acquired RGB color space values to spectral radiance, spectral reflectivity, absorption, scattering, CIELAB color coordinates, CIELAB XYZ tristimulus values, or any units of the CIE color space to normalize to spectroradiometric accuracy.

At 506, the converted image data may be compared to spectral radiance, spectral reflectivity, absorption, scattering, CIELAB color coordinates, CIELAB XYZ tristimulus values, or any units of the CIE color space information regarding master shade specimens that are contained in a database. For example, the shade selection program may reference master shade specimens that include Kerr Herculite Ultra (Kerr Corporation, Orange, Calif. USA) and Estelite Omega (Tokuyama Dental America, Encinitas, Calif. USA) composite disc shaped samples. Measurements of the radiant energy associated with the specimens taken directly or via the regression model may be compiled into the database which is provided locally to the user or remotely as described with reference to FIG. 11.

At 508, the shade selection program selects a shade in the database that best matches the acquired image data associated with the region of interest. The shade selection program attempts to select a shade having a CIEDE2000=0 as a result of a query with the same target and backing shade. The null hypothesis for this objective was as follows: There is no difference in the CIEDE2000 color differences in the shade selection output between the direct method and the method using regression estimates. The model developed in accordance with the operational flow 100 may be used by the selection program to select the shade that would result in the lowest CIEDE2000 color difference for the specific target and backing, as well as to indicate perceptibility and acceptability of the proposed shade match.

At 510, the selected shade is presented in a user interface to a user. Additionally or optionally, a second (or third, etc.) best choice may be presented.

The CIELAB values for the selected combinations of target and backing used as test scenarios for the shade selection program are shown in Table 7.

TABLE 7

CIELAB Values for the Selected Target and Backing Shades for the Test Scenarios in the Shade Selection Program

| Target Shade | Backing Shade | Target L* | Target a* | Target b* | Backing L* | Backing a* | Backing b* |
|---|---|---|---|---|---|---|---|
| A1 | A1 | 76.3 | 1.4 | 16.2 | 76.3 | 1.4 | 16.2 |
| A1 | B2 | 76.3 | 1.4 | 16.2 | 75.4 | −0.8 | 16.9 |
| A1 | D3 | 76.3 | 1.4 | 16.2 | 65.3 | 1.4 | 13.9 |
| B2 | A1 | 75.4 | −0.8 | 16.9 | 76.3 | 1.4 | 16.2 |
| B2 | B2 | 75.4 | −0.8 | 16.9 | 75.4 | −0.8 | 16.9 |
| B2 | D3 | 75.4 | −0.8 | 16.9 | 65.3 | 1.4 | 13.9 |
| D3 | A1 | 65.3 | 1.4 | 13.9 | 76.3 | 1.4 | 16.2 |
| D3 | B2 | 65.3 | 1.4 | 13.9 | 75.4 | −0.8 | 16.9 |
| D3 | D3 | 65.3 | 1.4 | 13.9 | 65.3 | 1.4 | 13.9 |
| 2M1 | 2M1 | 73.5 | 0.0 | 12.2 | 73.5 | 0.0 | 12.2 |
| 1M1 | 1M1 | 77.8 | −0.4 | 11.0 | 77.8 | −0.4 | 11.0 |
| 2L1.5 | 2L1.5 | 73.5 | −0.4 | 16.8 | 73.5 | −0.4 | 16.8 |

FIGS. 6-10 display the shade selection program results as Shade/Lot Number Versus CIEDE2000 Color Differences for different combinations of backing and target shades with acceptability and perceptibility thresholds. The FIGS are provided to show analysis between direct reflectance data and RGB data regressed to reflectance data to show the accuracy of the regression technique of the present disclosure as well as to verify the functionality of the shade selection program. Herculite Ultra shades are reported as the shade/lot number with a "D" following the shade representing dentin shades and Estelite Omega shades are reported as "EE" shade/lot number. A sample of the CIEDE2000 color differences between the selected shades and the target shade with perceptibility and acceptability thresholds using the shade selection program for test scenarios using the same Herculite Ultra backing shade (B) and target shade (T) is displayed in FIG. 6. In all three test scenarios utilizing the same target and backing shades, the CIEDE2000 between the output selected shade and the target shade was zero, thus verifying appropriate selections by the shade selection system.

Figure 7:
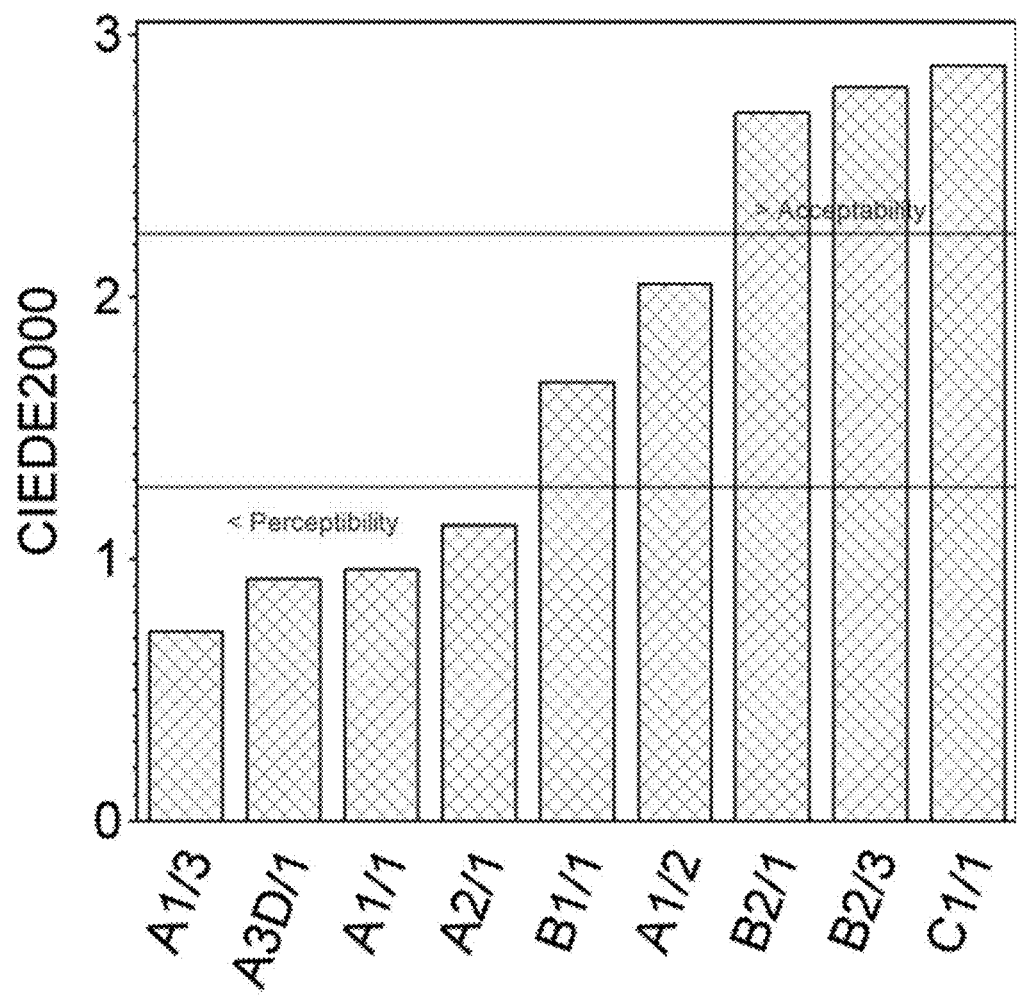
FIG. 7 illustrates a sample of the results of the shade selection program and the CIEDE2000 color differences between the selected shades and the target shade for Herculite Ultra composite resin shades when the target and backing are different in accordance with a direct method using reflectance data.
Figure 8:
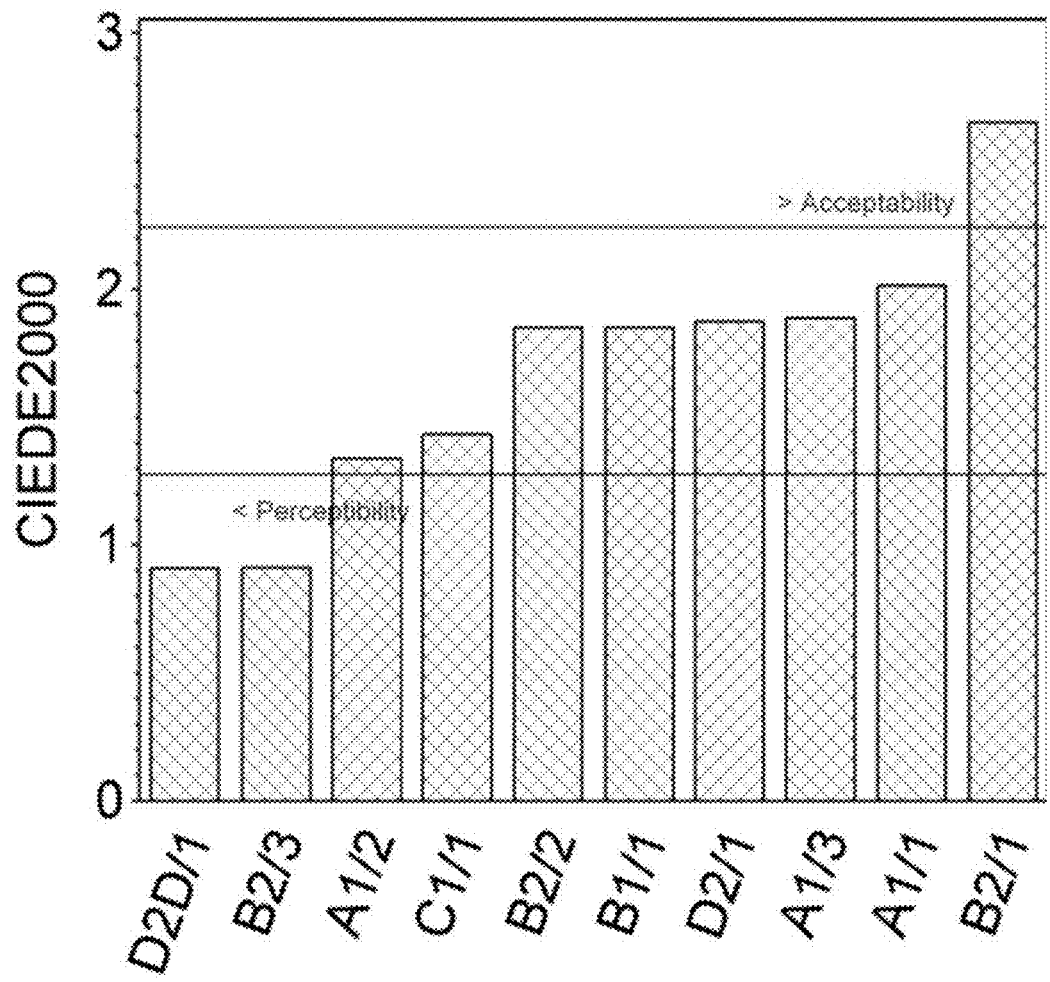
FIG. 8 illustrates a sample of the results of the shade selection program and the CIEDE2000 color differences with perceptibility and acceptability thresholds between these results and the target shade using the reflectance data from the Vita 3-D shade guide tabs when using the same target shade and same backing shade in accordance with a direct method using reflectance data.

FIG. 7 displays a sample of the results of the shade selection program and the CIEDE2000 color differences between the selected shades and the target shade for Herculite Ultra shades when the target and backing are different. Perceptibility and acceptability thresholds are indicated on these figures. FIG. 8 displays a sample of the results of the shade selection program and the CIEDE2000 color differences with perceptibility and acceptability thresholds between these results and the target shade using the reflectance data from the Vita 3-D shade guide tabs when using the same target shade and same backing shade.

Figure 9:
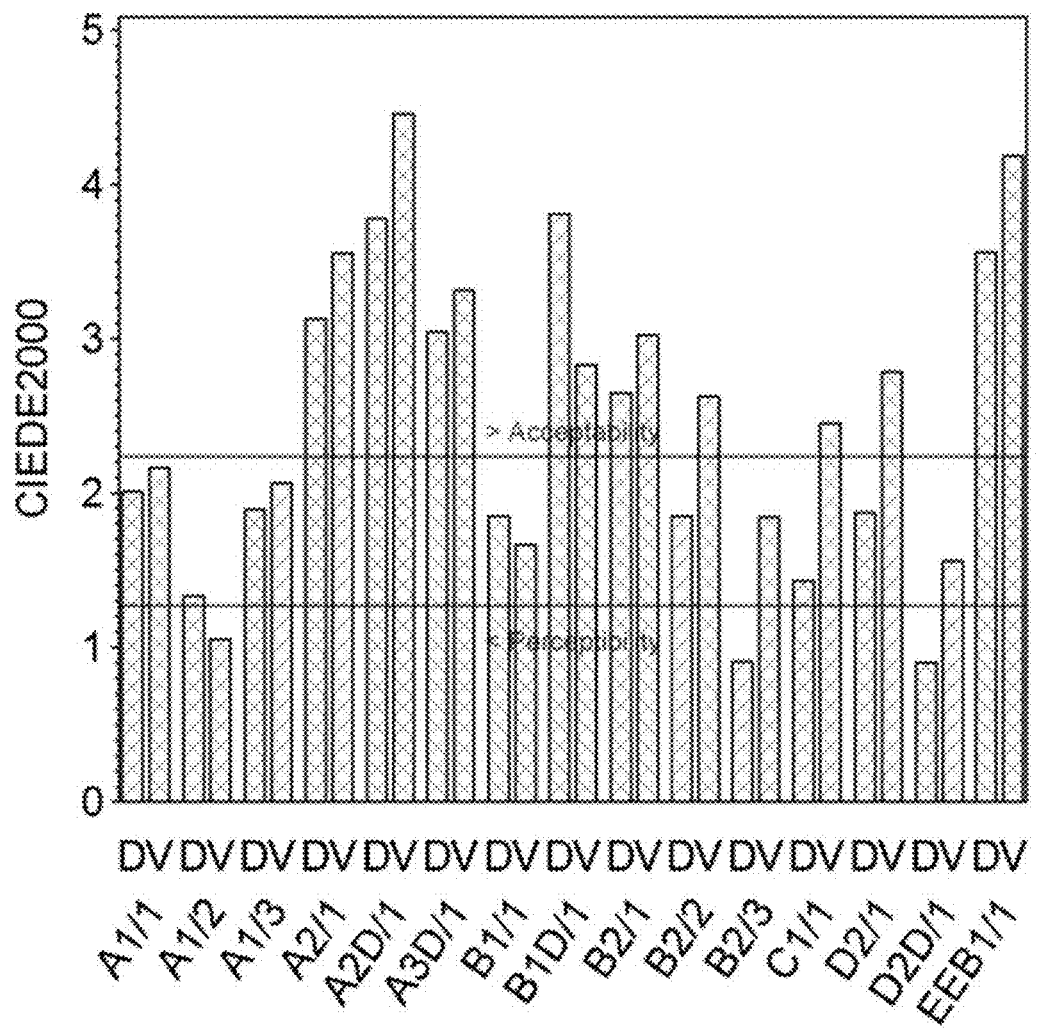
FIG. 9 illustrates a sample of the CIEDE2000 color difference pairs from the shade selection program for the selected shades when the shade selection program uses direct reflectance data (D) and when it uses RGB data via regression to reflectance data (V) for only one VITA 3-D shade guide tab.
Figure 10:
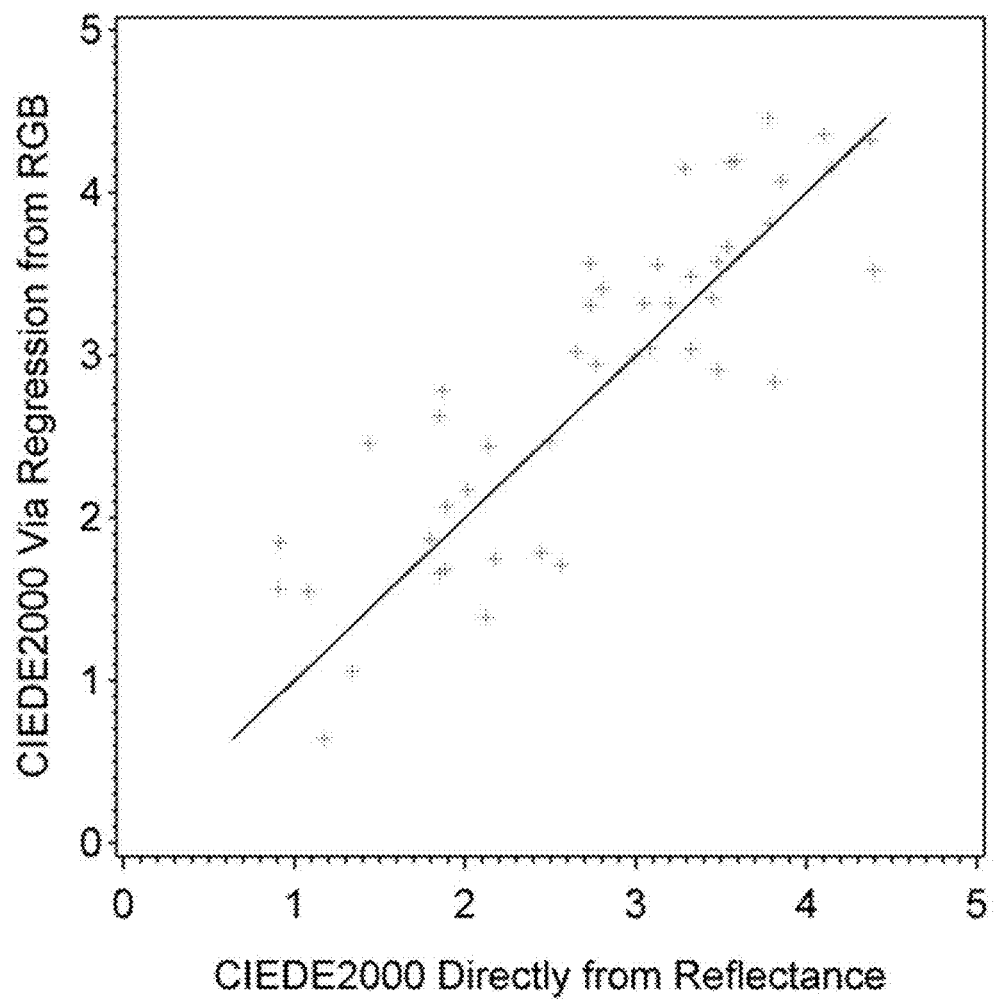
FIG. 10 illustrates analysis by a paired t-test for the direct and via regression methods.

A total of 46 pairs of color differences were obtained where the CIEDE2000 color differences by both of the two methods was less than 4.5, which is double the acceptability level that was used. Of these 46 pairs, a sample of the CIEDE2000 color difference pairs from the shade selection program for the selected shades are shown in FIG. 9 when the shade selection program uses direct reflectance data (D) and when it uses RGB data via regression to reflectance data (V) for only one VITA 3-D shade guide tab. When all 46 pairs of color differences where the CIEDE2000 color differences by both of the two methods was less than 4.5 were analyzed by the paired t-test, the probability of a greater |t| was <0.001. FIG. 10 shows all of these 46 pairs for the direct and via regression methods.

Because the best color match may involve color matching by layering alone, color adjustment potential can be thought of as an optical compensation for an error in layering. Because of this flexibility, a color match through layering has a certain range of color adjustment potential or blending that will allow for a less than perfect color match by layering alone. This present disclosure includes a mathematical model for the optical phenomenon of color adjustment potential or blending that describes and quantifies the amount of blending present. A clinical model was developed that simulated the scenario of a G.V. Black Class I, III, or V cavity preparation with a backing and surrounding material. Samples to simulate the blending effect were fabricated using a template of 12 mm diameter for the outer circle and 4 mm diameter for the inner circle. The samples had an outer thickness of 4 mm, an inner thickness of 2 mm, and a backing thickness for the inner segment of 2 mm. Specimens were sanded to achieve uniform thickness and to remove the outer matrix rich surface layer. The final measurements of the outer, inner, and backing to the inner thicknesses were taken. Radiant energy of the specimens was measured using the spectroradiometer at variable distances from the center in 1 mm increments on black and white backings. R0 was defined as the center of the specimen and +/−1 was defined as R1, +/−2 was defined as R2, and +/−3 was defined as R3. Absolute reflectance was calculated in the same manner as previously described. Theoretical predictions of absorption and scattering taking into consideration single and double layers where relevant were calculated by a least squares regression model of absorption and scattering using Kubelka-Munk Theory. These theoretical values were obtained using the characterized shades from the non-blended samples. The theoretical predictions due to layering effects were defined as TI and TO for the inner and the outer shades respectively. Differences in reflectance as well as color differences between theoretical and measured values were calculated. Color differences between the measured and predicted values at infinite thickness were calculated using the CIEDE2000 color difference formula.

Overall color difference between the outer and inner material was defined as having two components, layering and blending. It follows that the overall color difference of a translucent material in a surrounding material on an opaque backing equals the color difference due to layering minus the color difference due to blending. An overall color difference between the inner and the outer was defined as $\Delta E$ R3:R0. The color difference due to layering was then defined as $\Delta E$ TO:TI. In order to determine the color difference due to blending effects alone, the overall color difference ($\Delta E$ R3:R0) could be subtracted from the color difference due to layering ($\Delta E$ TO:TI). This difference mathematically describes blending that occurs due to the same optical phenomenon that takes place in edge effects. This mathematical model was developed using the following equations:

Color Difference=color difference$_{layering}$−color difference$_{blending}$

Color Difference=$\Delta ER3:R0$ color difference$_{layering}$=$\Delta ETO:TL$ color difference$_{blending}$=$\Delta ETO:TL-\Delta ER3:R0$ A variation on the color difference due to blending was used that considers only the larger outside influence on the inner material defined and determined as:

color difference$_{blending}$=$\Delta ETL:R0$

The Herculite Ultra shades used for the blending studies were selected to follow an equal distribution across the lightness scale using a Vita shade guide. CIE L*, a*, and b* values and availability of particular shades were also taken into consideration in order to optimize range of color. Three samples of each inner and outer combination of Herculite Ultra shades A1, B2, and D3 were fabricated and measured. Three samples of outer Herculite Ultra shades A1, B2, and D3 with inner Estelite Omega shade A1 were also fabricated and measured in the same manner.

The output of the shade selection program indicates the color difference that would result from all selections and suggests the selection with the lowest color difference. Although this shade selection program was developed using dental composite resins, the same system design can be used for color matching any translucent dental material to the natural dentition or any translucent material to a material of interest. This system could be easily modified to include suggestions for multiple layers and functions optimally with a very inclusive database of absorption and scattering information as well as to include concepts of blending that would make the color match even more accurate.

A shade selection program was designed and developed that depends on Kubelka-Munk layering to create the entire color match. Within this program, ranks of shades are given in order based on the least CIEDE2000 color difference between the resulting shade and the target shade. Concepts of color adjustment potential contribute then in a positive way to creating a better color match and can adjust for error in color selection by layering alone. Test scenarios indicated a systematic and accurate shade selection system when using the same target and backing shades. Most scenarios of backing and target combinations gave at least one option that was beneath the acceptability threshold indicating a clinically acceptable shade match. Many test scenarios indicated options that were beneath the perceptibility threshold indicating a very accurate process of shade selection. The clinically relevant RGB image data displays a translation to reflectance data that generally has little variability. This concept is imperative to making this process clinically applicable.

Example Apparatus

Figure 11:
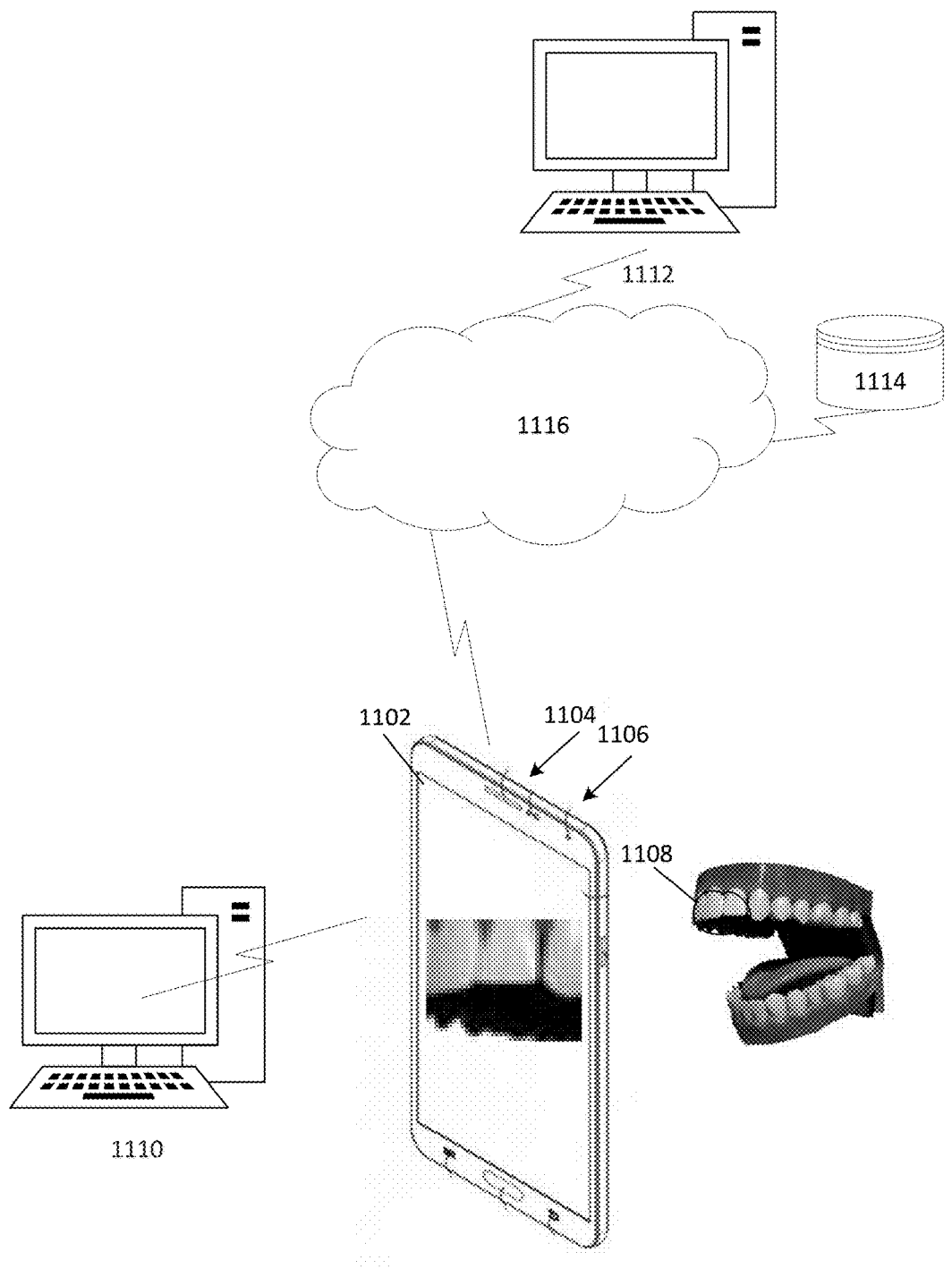
FIG. 11 illustrates an optical imaging system that may be used for analyzing digital images and matching craniofacial and dental material to a patient.

Referring to FIG. 11, an optical imaging system may be used for analyzing digital images and matching craniofacial and dental material to a patient. An imaging device 1102 illuminates an area of interest, such as a tooth. The imaging device 1102 may be a digital camera, smartphone, tablet or other handheld device that includes an optical sensor 1104 (e.g., a CMOS or CCD sensor) and an illumination source 1106 (e.g., a laser or LED). The imaging device 1102 may be configured with suitable optics such that it can generate data on a region of interest 1108 by moving the imaging device 1102 such that it is within viewable area of the optics. For example, using the illumination source to illuminate the area of interest 1108, scattered light may be captured by the optical sensor, as described below.

The detected light may be processed using the device-dependent model, as described above, to quantify and normalize captured RGB data. For example, the imaging device 1102 may process RGB data collected by the optical sensor signals from the detectors, for example, by demodulating the detected signals, to generate data indicative of the detected magnitude of light from each illumination source. The imaging device 102 may be configured to quantify absorbing and spectral radiance, spectral reflectivity, absorption, scattering, CIELAB color coordinates, CIELAB XYZ tristimulus values, or any units of the CIE color space of the region of interest 1108 as well as characteristics based on the extracted data. Alternatively or additionally, the imaging device 1102 may be configured to send reduced or raw data to a remote processor for further processing to determine generated data characterizing the region of interest 1108. To transmit data, for example, the imaging device 1102 may employ a wireless communication module that allows wireless transmission of information between the imaging device 1102 and a local terminal 1110 or a cloud-based provider 1112 over a network connection 1116, such as the Internet.

In accordance with the division of functions between the terminal 1110 and/or cloud provider 1112 and the imaging device 1102, the terminal 1110 or cloud provider 1112 may be configured to perform further processing on the data acquired by the imaging device 1102. For example, terminal 1110 or cloud provider 1112 may apply the model to quantify and normalize RGB data obtained by the optical sensor and correlate it to precharacterized shades of translucent materials that are maintained in a database 1114. The terminal 1110 and cloud provider 1112 may also communicate details of the analysis to a user. For example, the terminal 1110 may provide a user interface that displays an indication of the shade (or alternative shades) of translucent material that best matches the area of interest.

The present disclosure has been described herein with regard to several implementations. However, it will be obvious to persons skilled in the art that a number of variations and modifications can be made without departing from the scope of the disclosure as described herein.

What is claimed is:

1. A method for color matching of translucent materials, comprising:

acquiring one or more images of a region of interest using a digital imaging device;

applying regression modeling to convert an acquired Red, Green and Blue (RGB) color space value to spectral radiance, spectral reflectivity, absorption, scattering, CIELAB color coordinates, CIELAB XYZ tristimulus values, or any units of the CIE color space while to normalize the RGB color space value to spectroradiometric accuracy;

comparing the converted values to master shade specimen data contained in a database;

selecting one of the master shade specimens that best matches the spectral radiance, spectral reflectivity, absorption, scattering, CIELAB color coordinates, CIELAB XYZ tristimulus values, or any units of the CIE color space value by having a smallest CIEDE2000 color difference relative to the CIELAB color space value of the region of interest, the color difference being further determined in accordance with blending effects by subtracting the overall color difference ($\Delta E$ R3:R0) from the color difference due to layering ($\Delta E$ TO:TL) in accordance with the relationships:

Color Difference=color difference$_{layering}$−color difference$_{blending}$

Color Difference=$\Delta E$ R3:R0 color difference$_{layering}$=$\Delta E$ TO:TL color difference$_{blending}$=$\Delta E$ TO:TL−$\Delta E$ R3:R0 wherein an overall color difference between an inner and an outer was defined as $\Delta E$ R3:R0, wherein a color difference due to layering is defined as $\Delta E$ TO:TL; and presenting an indication of the selected one of the master shade specimens to a user in a user interface.

2. The method of claim 1, further comprising comparing the normalized RGB value to spectral radiance, spectral reflectivity, absorption, scattering, CIELAB color coordinates, CIELAB XYZ tristimulus values, or any units of the CIE color space associated with the master shade specimens contained in a database and taking into consideration principles of Kubelka-Munk layering on a backing shade to create a target shade or desired shade.

3. The method of claim 2, wherein the master shade specimens include sample data from a translucent material of interest.

4. The method of claim 1, further comprising selecting a master shade specimen having a CIEDE2000=0 as a result of a query with a same target and backing shade.

5. The method of claim 1, wherein the best color match is obtained by layering different master shade specimen colors.

6. The method of claim 1, wherein the best color match is obtained by layering and then blending can compensate for error.

7. The method of claim 1, further comprising determining a color difference in accordance with blending with an outside influence on an inner material as:

color difference$_{blending}$=$\Delta E$ TL$_1$R0

8. The method of claim 1, further comprising providing suggestions for multiple layers to provide the best match.

9. The method of claim 1, further comprising:

ranking of shades based on the least CIEDE2000 color difference between the resulting shade and the target shade in accordance with Kubelka-Munk layering to create the color match.

* * * * *

UNITED STATES PATENT AND TRADEMARK OFFICE
CERTIFICATE OF CORRECTION

PATENT NO. : 10,387,746 B2
APPLICATION NO. : 15/587504
DATED : August 20, 2019
INVENTOR(S) : Melody Noelle Carney and William Michael Johnston Page 1 of 1

It is certified that error appears in the above-identified patent and that said Letters Patent is hereby corrected as shown below:

In the Specification

Column 1, Lines 17-19 replace the Government Support Clause with:
--This invention was made with government support under grant number DE014320 awarded by National Institutes of Health. The government has certain rights in the invention.--

Signed and Sealed this
Sixth Day of October, 2020

Andrei Iancu
*Director of the United States Patent and Trademark Office*